United States Patent [19]

Kühne et al.

[11] Patent Number: 4,670,441
[45] Date of Patent: Jun. 2, 1987

[54] THIOBARBITURIC ACID DERIVATIVES AND THEIR USE AS ANTHELMINTHICS

[75] Inventors: Manfred Kühne, Pfeffingen; Jean J. Gallay, Magden, both of Switzerland

[73] Assignee: Ciba-Geigy Corporation, Ardsley, N.Y.

[21] Appl. No.: 751,715

[22] Filed: Jul. 5, 1985

[30] Foreign Application Priority Data

Jul. 6, 1984 [CH] Switzerland ............... 3288/84

[51] Int. Cl.$^4$ .............. A61K 31/515; C07D 239/66; C07D 239/68
[52] U.S. Cl. ................. 514/270; 544/300; 544/301
[58] Field of Search ............ 544/300; 514/270

[56] References Cited

U.S. PATENT DOCUMENTS

| 3,961,061 | 6/1976 | Krämer et al. | 544/301 |
| 4,229,454 | 10/1980 | Beriger | 544/301 |
| 4,283,444 | 8/1981 | de Sousa et al. | 544/301 |
| 4,399,280 | 8/1983 | de Sousa et al. | 544/301 |
| 4,503,100 | 3/1985 | de Sousa et al. | 544/301 |

FOREIGN PATENT DOCUMENTS

| 0074335 | 3/1983 | European Pat. Off. | 544/301 |
| 105029 | 4/1984 | European Pat. Off. | |
| 102327 | 7/1984 | European Pat. Off. | |
| 2405732 | 8/1975 | Fed. Rep. of Germany | |
| 1464326 | 9/1977 | United Kingdom | |
| 2126582 | 3/1984 | United Kingdom | 544/301 |

OTHER PUBLICATIONS

American J. Vet. Res., vol. 37, No. 12, pp. 1515, 1516 (Dec. 76).
American J. Vet. Res., vol. 38, No. 6, pp. 807, 808 (Jun. 77).
American J. Vet. Res. vol. 38, No. 8, pp. 1247, 1248 (Aug. 77).
American J. Vet. Res., vol. 38, No. 9, pp. 1464, 1426 (Sep. 77).

Primary Examiner—Donald G. Daus
Assistant Examiner—Stephan M. Kapner
Attorney, Agent, or Firm—Edward McC. Roberts; Meredith C. Findlay

[57] ABSTRACT

The invention relates to novel 5-phenylcarbamoylthiobarbituric acid derivatives of the general formula

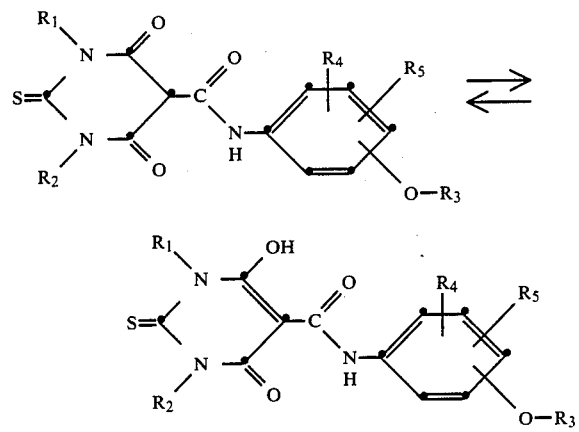

wherein
$R_1$ and $R_2$ are each independently $C_1$–$C_5$alkyl or methoxy,
$R_3$ is unsubstituted phenyl, unsubstituted pyridyl, or phenyl which is substituted by 1 to 3 identical or different members selected from the group consisting of $C_1$–$C_5$alkyl, $C_1$–$C_4$cyanoalkyl, halogen, nitro and $C_1$–$C_5$haloalkyl containing 1 to 5 halogen atoms, or is pyridyl which is substituted by 1 to 3 identical or different members selected from the group consisting of $C_1$–$C_5$alkyl, halogen, nitro and $C_1$–$C_5$haloalkyl containing 1 to 5 halogen atoms and
$R_4$ and $R_5$ are each independently hydrogen, halogen, $C_1$–$C_5$alkyl, $C_1$–$C_2$haloalkyl containing 1 to 3 halogen atoms, or are $C_1$–$C_3$-alkoxy or nitro,
and to the tautomers and salts thereof, as anthelmintics.

The compounds may be used by themselves or together with suitable carriers and further adjuvants for controlling helminths which are parasites of animals.

13 Claims, No Drawings

THIOBARBITURIC ACID DERIVATIVES AND THEIR USE AS ANTHELMINTHICS

The present invention relates to novel 5-phenylcarbamoylthiobarbituric acid derivatives having anthelmintic activity, to compositions containing these compounds as active ingredients, and to the use of said compounds or compositions for controlling helminths, in particular nematodes, cestodes and trematodes in domestic animals and productive livestock, especially in mammals.

The invention further relates to the preparation of the novel compounds and of compositions containing them and to intermediates which can be used in the preparation of said novel compounds.

Specifically, the present invention relates to novel compounds of the general formula I

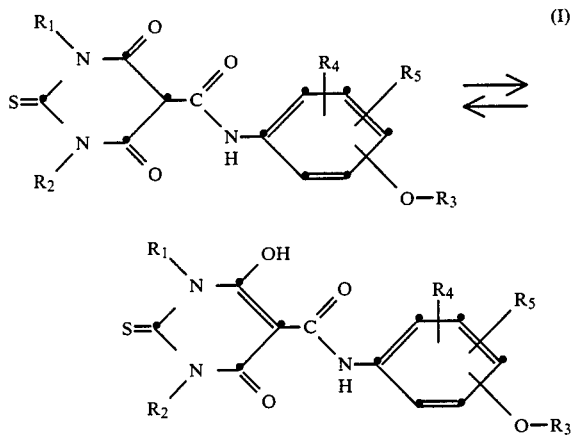

wherein
$R_1$ and $R_2$ are each independently $C_1-C_5$alkyl or methoxy,
$R_3$ is unsubstituted phenyl, unsubstituted pyridyl, or phenyl which is substituted by 1 to 3 identical or different members selected from the group consisting of $C_1-C_5$alkyl, $C_1-C_4$cyanoalkyl, halogen, nitro and $C_1-C_5$haloalkyl containing 1 to 5 halogen atoms, or is pyridyl which is substituted by 1 to 3 identical or different members selected from the group consisting of $C_1-C_5$alkyl, halogen, nitro and $C_1-C_5$haloalkyl containing 1 to 5 halogen atoms and
$R_4$ and $R_5$ are each independently hydrogen, halogen, $C_1-C_5$alkyl, $C_1-C_2$haloalkyl containing 1 to 3 halogen atoms, or are $C_1-C_3$alkoxy or nitro,
and to the tautomers and salts thereof.

Preferred compounds of formula I are those belonging to one of the groups of compounds listed below, wherein:

(a) $R_1$ and $R_2$ are each independently $C_1-C_5$alkyl or methoxy, $R_3$ is unsubstituted phenyl, unsubstituted pyridyl, or phenyl which is substituted by 1 to 3 identical or different members selected from the group consisting of $C_1-C_5$alkyl, $C_1-C_4$cyanoalkyl, halogen, nitro and $C_1-C_5$haloalkyl containing 1 to 5 halogen atoms, or is pyridyl which is substituted by 1 to 3 identical or different members selected from the group consisting of $C_1-C_5$alkyl, halogen, nitro and $C_1-C_5$haloalkyl containing 1 to 5 halogen atoms and $R_4$ and $R_5$ are each independently hydrogen, halogen, $C_1-C_5$alkyl, $C_1-C_2$haloalkyl containing 1 to 3 halogen atoms, or are nitro;

(b) $R_1$ is methyl, ethyl or methoxy, $R_2$ is methyl, $R_3$ is unsubstituted phenyl, unsubstituted pyridyl, or phenyl which is substituted by 1 or 2 identical or different members selected from the group consisting of $C_1-C_5$alkyl, $C_1-C_4$cyanoalkyl, halogen, nitro and $C_1-C_5$haloalkyl containing 1 to 3 halogen atoms, or is pyridyl which is substituted by 1 or 2 identical or different members selected from the group consisting of $C_1-C_5$alkyl, halogen, nitro and $C_1-C_5$haloalkyl containing 1 to 3 halogen atoms and $R_4$ and $R_5$ are each independently hydrogen, $C_1-C_5$alkyl or halogen;

(c) $R_1$ is methyl or methoxy, $R_2$ is methyl, $R_3$ is phenyl which is substituted by methyl, cyanomethyl, chlorine, fluorine or trifluoromethyl, or is pyridyl which is substituted by methyl, chlorine, fluorine or trifluoromethyl and $R_4$ and $R_5$ are each independently hydrogen, $C_1-C_3$alkyl, chlorine or nitro;

(d) $R_1$ is methyl or methoxy, $R_2$ is methyl, $R_3$ is phenyl which is substituted by methyl, cyanomethyl, chlorine or trifluoromethyl, or is pyridyl which is substituted by methyl, chlorine or trifluoromethyl and $R_4$ and $R_5$ are each independently hydrogen or $C_1-C_3$alkyl and the radical —O—$R_3$ is in the 2- or 4-position; and (e) $R_1$ is methyl or ethyl, $R_2$ is methyl, $R_3$ is phenyl which is substituted by 1 or 2 identical or different members selected from the group consisting of cyanomethyl, fluorine, chlorine, nitro and trifluoromethyl, or is 2-pyridyl which is substituted by 1 to 2 identical or different members selected from the group consisting of fluorine, chlorine, nitro and trifluoromethyl, $R_4$ is hydrogen, chlorine, methyl, isopropyl or methoxy and $R_5$ is hydrogen, chlorine or methyl, including the triethylamine salts thereof.

Particularly interesting compounds are those of formula I, wherein each of $R_1$ and $R_2$ is methyl, $R_3$ is phenyl which is substituted by 1 or 2 identical or different members selected from the group consisting of chlorine and trifluoromethyl, or is 2-pyridyl which is substituted by 1 or 2 identical or different members selected from the group consisting of chlorine and trifluoromethyl, $R_4$ is hydrogen, methyl, isopropyl or methoxy and $R_5$ is hydrogen or methyl, the radical —$OR_3$ being in meta- or para-position to the nitrogen atom of the carbamoyl group, and a triethylamine salt thereof, and especially those compounds of formula I, wherein each of $R_1$ and $R_2$ is methyl, $R_3$ is phenyl which is substituted by 1 or 2 identical or different members selected from the group consisting of chlorine and trifluoromethyl, or is 2-pyridyl which is substituted by 1 or 2 identical or different members selected from the group consisting of chlorine and trifluoromethyl, $R_4$ is hydrogen or methoxy and $R_5$ is hydrogen, the radical —$OR_3$ being in meta- or para-position to the nitrogen atom of the carbamoyl group.

Preferred individual compounds are:
1,3-dimethyl-5-[2-isopropyl-4-(5-trifluoromethylpyrid-2-yloxy)phenylcarbamoyl]-2-thiobarbituric acid,
1,3-dimethyl-5-[4-(5-trifluoromethylpyrid-2-yloxy)-phenylcarbamoyl]-2-thiobarbituric aicd, triethylamine salt,
1,3-dimethyl-5-[4-(3-chloro-5-trifluoromethylpyrid-2-yloxy)phenylcarbamoyl]-2-thiobarbituric acid,
1,3-dimethyl-5-[2,6-dimethyl-4-(5-trifluoromethylpyrid-2-yloxy)phenylcarbamoyl]-2-thiobarbituric acid,
1,3-dimethyl-5-[4-(3,5-dichloropyrid-2-yloxy)phenylcarbamoyl]-2-thiobarbituric acid, and especially 1,3-dimethyl-5-[4-(5-trifluoromethylpyrid-2-yloxy)-phenylcarbamoyl]-2-thiobarbituric acid, 1,3-dimethyl-5-[4-(4-trifluoromethylphenoxy)phenylcarbamoyl]-2-thiobarbituric acid, 1,3-dimethyl-5-[4-(3-trifluoromethylphenoxy)phenylcarbamoyl]-2-thiobarbituric acid, 1,3-dimethyl-5-[4-methoxy-3-(2-chloro-4-trifluoromethylphenoxy)phenylcarbamoyl]-2-thiobarbituric acid, 1,3-dimethyl-5-[3-methoxy-4-(2-chloro-4-trifluoromethylphenoxy)phenylcarbamoyl]-2-thiobarbituric acid and 1,3-dimethyl-5-[4-methoxy-3-(3,5-dichloropyrid-2-yloxy)phenylcarbamoyl]-2-thiobarbituric acid.

The salts of compounds of formula I comprise for example the alkali metal salts, ammonium salts or amine salts, with the sodium, potassium, ammonium or alkylamine salts being preferred. Trialkylamine salts are preferred wherein each of the alkyl groups independently contains 1 to 4 carbon atoms, especially triethylamine salts. Within the scope of formula I, alkyl as an independent group or as moiety of a group $R_1$ to $R_5$ will be understood as meaning straight chain and branched alkyl groups. Examples of such groups are methyl, ethyl and the isomers of the propyl, butyl and pentyl group. Halogen denotes fluorine, chlorine, bromine or iodine, with fluorine or chlorine being preferred.

Alkoxy groups are ethoxy, n-propoxy, isopropoxy and, preferably, methoxy.

The compounds of formula I are prepared by (a) reacting an ester of formula II

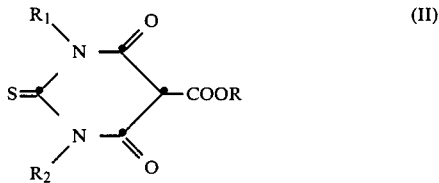

with an aniline derivative of formula III

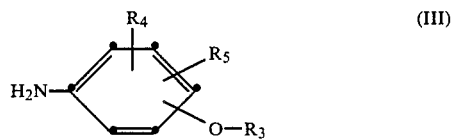

in which formulae R is $C_1$-$C_4$alkyl, unsubstituted phenyl or phenyl which is substituted by nitro and the radicals $R_1$ to $R_5$ are as defined for formula I, or (b) reacting a substituted thiobarbituric acid of formula IV

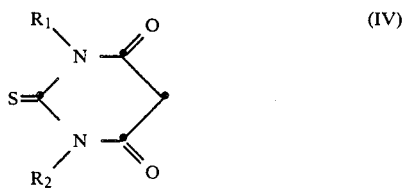

with a substituted phenylisocyanate of formula V

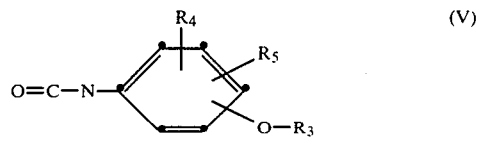

in which formulae the radicals $R_1$ to $R_5$ are as defined for formula I, or (c) reacting a substituted thiobarbituric acid of formula IV with a substituted benzoylazide of formula VI

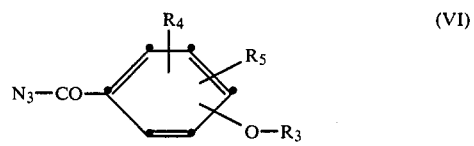

in which formulae the radicals $R_1$ to $R_5$ are as defined for formula I.

Variants (a) and (c) are carried out at reaction temperatures in the range from 50° to 250° C., preferably from 70° to 220° C. Variant (b) requires reaction temperatures in the range from 0° to 220° C., preferably from 0° to 200° C. Reactions (a), (b) and (c) are carried out under normal or elevated pressure and in the absence or, preferably, in the presence of solvents or diluents which are inert or which promote the reaction. In some cases the reactions are advantageously carried out in the presence of a base.

The salts of compounds of formula I are prepared by conventional neutralisation of the free acid with a base, in particular a physiologically acceptable base. Preferred salts are alkali metal salts such as sodium, potassium or lithium salts, as well as ammonium salts and trialkylamine salts, e.g. the preferred triethylamine salt. Neutralisation is effected in an inert polar solvent, e.g. an alkanol, an ester or an ethereal compound.

Examples of solvents or diluents suitable for the preparation of the compounds of the invention are ethers and ethereal compounds such as dialkyl ethers (diethyl ether, diisopropyl ether, tert-butylmethyl ether etc.), anisole, dioxane, tetrahydrofuran; aliphatic and aromatic hydrocarbons such as benzene, toluene, petroleum ether; halogenated hydrocarbons such as chlorobenzene, methylene chloride, chloroform, ethylene chloride, carbon tetrachloride, tetrachloroethylene; nitriles such as acetonitrile and propionitrile; N,N-dialkylated amides such as dimethylformamide; dimethyl sulfoxide; ketones such as acetone, diethyl ketone and methyl ethyl ketone; and mixtures of such solvents with each other.

Suitable bases are organic and inorganic bases, e.g. preferably tertiary amines such as trialkylamines (trimethylamine, triethylamine or tripropylamine), pyridine and pyridine bases (e.g. 4-dimethylaminopyridine or 4-pyrrolidylaminopyridine), picolines and lutidines, as well as oxides, hydroxides, carbonates and bicarbonates of alkali metals and alkaline earth metals (e.g. CaO, BaO, NaOH, KOH, Ca(OH)$_2$, KHCO$_3$, NaHCO$_3$, Ca(HCO$_3$)$_2$, K$_2$CO$_3$ or Na$_2$CO$_3$), and also acetates such as CH$_3$COONa or CH$_3$COOK. Further suitable bases are alkali alcoholates, e.g. sodium methylate, sodium propylate, potassium tert-butylate or sodium methylate.

It is advantageous to add the base in 10 to 100% of the equimolar amount, based on the reactants.

In some cases it may be of advantage to carry out the reaction in an inert gas atmosphere. Suitable inert gases are e.g. nitrogen, helium, argon or carbon dioxide.

Reaction of the free acid of formula I with bases gives the salts which also fall within the province of the invention.

The compounds of formula I may exist in different tautomeric forms, viz. in the keto or enol form or in a mixture of these forms. The present invention relates both to the individual tautomers and to their mixtures, as well as to the salts of each of these forms and to the preparation thereof.

The preparatory process described, including all variants (a), (b) and (c), constitutes an object of the present invention.

The starting materials in variants (a), (b) and (c) are either known (q.v. e.g. German Offenlegungsschrift No. 2 936 457) or, if novel, they can be prepared by a process analogous to that for preparing the known substances.

Novel starting materials are isocyanates of formula Va

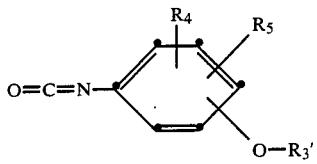

wherein $R_3'$ is unsubstituted pyridyl or pyridyl which is substituted by 1 to 3 identical or different members selected from the group consisting of $C_1$-$C_5$alkyl, halogen, nitro and $C_1$-$C_5$haloalkyl containing 1 to 5 halogen atoms and $R_4$ and $R_5$ are each independently hydrogen, halogen, $C_1$-$C_5$alkyl, $C_1$-$C_2$haloalkyl containing 1 to 3 halogen atoms, or are $C_1$-$C_3$alkoxy or nitro.

The novel isocyanates of formula Va are prepared by known processes (q.v. Houben-Weyl, Method. d. Organ. Chemie, Twitchett, H. J., Chem. Soc. Rev. 3, (1974), 209–230) as follows:

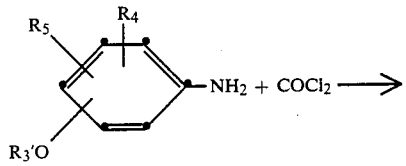

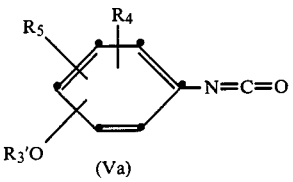

in which formulae $R_3'$, $R_4$ and $R_5$ are as defined above for formula Va. The compounds of formulae Va and VIa constitute a further object of the present invention.

The reaction takes place in the temperature range from 50° to 150° C. in the presence of solvents or diluents which are inert or which promote the reaction.

the azides of formula VIa are prepared by known processes (q.v. Patai, Chemistry of the Acido Group, pp. 503–554 (1971), Interscience Publ., New York) as follows:

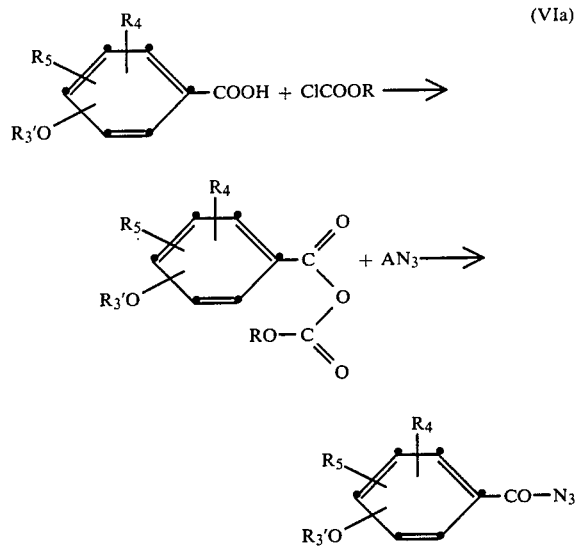

in which formulae $R_3'$, $R_4$ and $R_5$ are as defined above for formula Va, R is a $C_1$-$C_4$alkyl group, an unsubstituted phenyl group or a phenyl group which is substituted by nitro and A is alkali.

The reaction takes place in the temperature range from $-50°$ C. to 30° C. in the presence of solvents or diluents which are inert or which promote the reaction.

Examples of solvents or diluents suitable for use in the above processes for the preparation of compounds of formulae Va and VIa are: ethers and ethereal compounds such as dialkyl ethers (diethyl ether, diisopropyl ether, tert-butylmethyl ether etc.), anisole, dioxane, tetrahydrofuran; aliphatic and aromatic hydrocarbons such as benzene, toluene, petroleum ether; halogenated hydrocarbons such as chlorobenzene, methylene chloride, chloroform, ethylene chloride, carbon tetrachloride, tetrachloroethylene; nitriles such as acetonitrile and propionitrile; N,N-dialkylated amides such as dimethylformamide; dimethyl sulfoxide; ketones such as acetone, diethyl ketone and methyl ethyl ketone; and mixtures of such solvents with each other.

Also novel are the starting materials of formula II

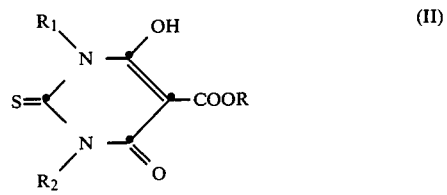

wherein R is $C_1$-$C_4$alkyl, an unsubstituted phenyl group or a phenyl group which is substituted by nitro and $R_1$ and $R_2$ are as defined for formula I. These compounds likewise constitute an object of the present invention.

Compounds of formula II are prepared by reacting a thiobarbituric acid derivative of formula IV

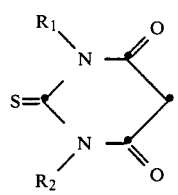

with a chloroformate of the formula

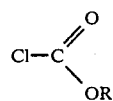

in which formulae $R_1$, $R_2$ and R are as defined above, in the presence of a base, e.g. pyridine.

The reaction is carried out in the temperature range from $-50°$ C. to $50°$ C., preferably from $0°$ to $30°$ C., in the absence or presence of solvents or diluents which are inert or which promote the reaction. In the absence of such solvents or diluents, the base employed will serve as sole solvent. Suitable solvents and diluents are e.g. those described above as suitable for use in variants (a), (b) and (c).

It is particularly advantageous to prepare compounds of formula I of the invention by a process in which the different reactions are carried out in the same vessel. Said process comprises first forming, as described above, a compound of formula II by reacting a compound of formula IV with a chloroformate and subsequently reacting said compound of formula II, without isolation, with a compound of formula III in accordance with the above process variant (a) as follows:

As is generally known, among the endoparasites which occur in warm-blooded animals, the helminths cause severe damage to the animals they infest. The damage caused by helminthiases can assume significant economic proportions whenever herds of cattle fall victim to chronic and, in particular, epidemic infestation. In infected animals, such damage takes the form inter alia of diminution of useful performance, weakened resistance to further diseases and increased mortality. Particularly dangerous helminth infestations are caused by helminths parasitising in the gastrointestinal tract and other organs and may occur for example in ruminants such as cattle, sheep and goats, as well as horses, pigs, poultry, deer, dogs and cats.

Throughout the present specification, the termm "helminths" will be understood as meaning in particular parasitic worms which belong to the phyla Platyhelminthes (cestodes, trematodes) and Nemathelminthes (nematodes and related species), i.e. cestodes. trematodes and nematodes of the gastrointestinal tract and other organs (e.g. liver, lungs, kidneys, lymphatic vessels, blood etc.).

It is therefore of great importance to develop therapeutic agents which are suitable for controlling helminths in all development stages and to prevent attack by these parasites.

Although a range of compounds having anthelminthic activity are known and have been proposed for controlling the different helminth species, they are not entirely satisfactory, either because it is not possible to exploit their activity spectrum fully when administered in well tolerated doses or because they exhibit undesirable side-effects or characteristics when administered in therapeutic doses. In this regard, the increasing resistance being encountered at the present time to specific

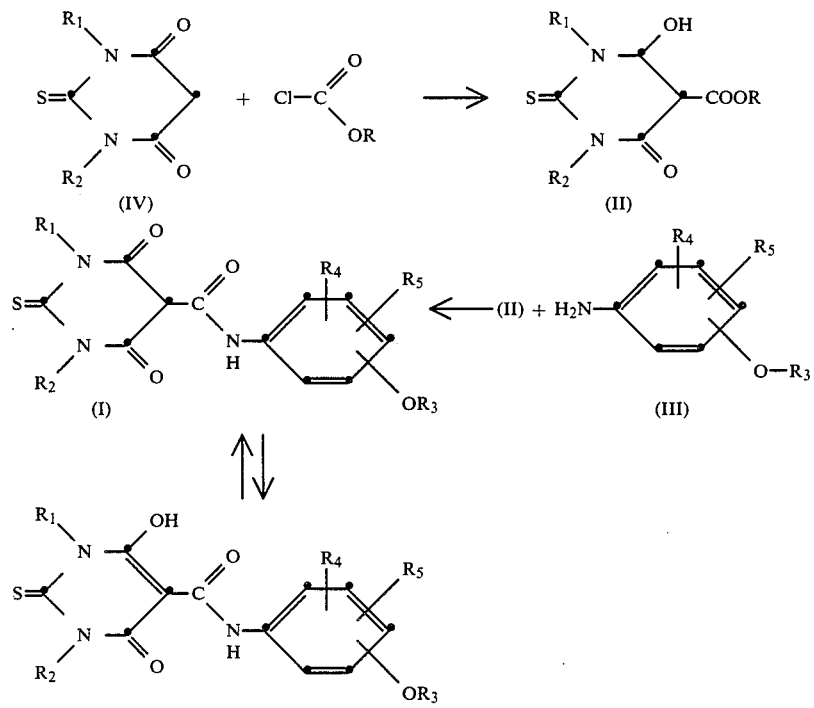

Examples of compounds of formulae III, V/Va and VI/VIa which can be prepared by the methods described above are shown in Tables 1, 2 and 3.

classes of compound is an ever more significant factor. For example, the prior art compound "albendazole" (British patent specification No. 1 464 326; Am. J. Vet. Res. 38, 1425–1426 (1977); Am. J. Vet. Res. 37, 1515–1516 (1976); Am. J. Vet. Res. 38, 807–808 (1977); Am. J. Vet. Res. 38, 1247–1248 (1977)) has only a limited activity spectrum as anthelmintic when administered to ruminants. Its activity e.g. against benzimidazole-resistant nematodes and adult liver flukes is completely inadequate. In particular, the pathologically important immature migratory forms of the last mentioned parasites are not attacked when the compound is administered in doses which are tolerated by the host animal.

Further, German Offenlegungsschrift 2 405 732 discloses amidocarbonylthiobarbituric acid derivatives as ecto- and endo-parasiticides.

The novel compounds of formula I of the invention differ structurally in character from the barbituric acid derivatives known from the above-mentioned publication. Surprisingly, it has been found that the novel compounds possess a broad activity spectrum against helminths such as nematodes, cestodes and trematodes parasitising in the animal organism, in particular in mammals, said activity preferably being directed against nematodes.

A particular feature of the compounds of formula I is that they are surprisingly well tolerated by warm-blooded animals, which tolerance makes them superior to the known thiobarbituric acid derivatives. As the novel compounds are tolerated without symptoms by the animals receiving the medication even at higher doses, their practical handling in the treatment of animals infected with helminths is thereby greatly facilitated.

The novel compounds of formula I of the invention are suitable e.g. for controlling parasitic nematodes of the orders (according to the classification of K. I. Skrajabin)
Rhabditida
Ascaridida
Spirurida
Trichocephalida
or for controlling cestodes of the orders (according to the classification of Wardle and McLeod)
Cyclophyllidae
Pseudophyllidae
or for controlling trematodes of the order
Digenea
in domestic animals and productive livestock such as cattle, sheep, goats, horses, pigs, deer, cats, dogs and poultry. The compounds of formula I can be administered to the animals in both individual and repeated doses. Depending on the species of animal, the individual doses are preferably administered in amounts ranging from 1 to 20 mg per kg of body weight. A better activity is sometimes achieved by protracted administration, or lower doses may suffice.

The compositions of this invention are prepared by bringing the compounds of formula I into contact with liquid and/or solid formulation adjuvants by stepwise mixing and/or grinding such that the formulation is able to exert its anthelmintic activity in optimum manner in accordance with the mode of application.

The formulation steps may be complemented by kneading, granulating and, if desired, pelleting.

Suitable formulation adjuvants are for example solid carriers, solvents and, optionally, surface-active compounds (surfactants).

The following formulation adjuvants are employed for preparing the compositions of the invention; solid carriers, e.g. kaolin, talc, bentonite, common salt, calcium phosphate, carbohydrates, cellulose powder, cottonseed meal, polyethylene glycol ether, optionally binders such as gelatin, soluble cellulose derivatives, if desired with the addition of surface-active compounds such as ionic or non-ionic dispersants; natural mineral fillers such as calcite, montmorillonite or attapulgite. To improve the physical properties it is also possible to add highly dispersed silicic acid or highly dispersed adsorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant material.

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils and epoxidised vegetable oils such as epoxidised coconut oil or soybean oil; or water.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$ alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the aliphatic hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$ alkyl radical and, as further sutstituents, unsubstituted or halogenated lower alkyl, benzyl or hydroxy-lower alkyl radicals. The salts are preferably in the form of halides, methylsulfates or ethylsulfates, e.g. stearyl-trimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ridgewood, N.J. 1980, and Sisley and Wood, "Encyclopedia of Surface Active Agents", Chemical Publishing Co., Inc. New York, 1980.

Suitable binders for tablets and boluses are chemically modified natural polymers which are soluble in water or alcohol, e.g. starch, cellulose or protein derivatives (e.g. methyl cellulose, carboxymethyl cellulose, ethyl hydroxyethyl cellulose, proteins such as zein, gelatin and the like), as well as synthetic polymers such as polyvinyl alcohol, polyvinyl pyrrolidine etc. Tablets also contain fillers (e.g. starch, microcrystalline cellulose, sugar, lactose etc.), glidants and disintegrators.

If the anthelmintic compositions are in the form of feed concentrates, then suitable carriers are for example production feeds, cereal feeds or protein concentrates. In addition to the active ingredients, such feeds can contain additives, vitamins, antibiotics, chemotherapeutical agents or other pesticides, in particular bacteriostats, fungistats, coccidiostats or also hormone preparations, substances having anabolic action or other substances which promote growth, enhance the quality of the flesh of slaughter animals, or which are otherwise beneficial to the organism. If the compositions or the compounds of formula I contained therein are added direct to the solid or liquid feed, then the ready prepared feed contains the active ingredient preferably in a concentration of about 0.0005 to 0.02 percent by weight (5–200 ppm).

The compositions of the invention are administered to the animals to be treated perorally, parenterally or subcutaneously, and are in the form of solutions, emulsions, suspensions (drenches), powders, tablets, boluses and capsules.

The anthelmintic compositions of this invention usually contain 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

Whereas commercial products will be preferably formulated as concentrates, the end user will normally employ dilute formulations.

The compositions may also contain further ingredients such as stabilisers, antifoams, viscosity regulators, binders, tackifiers as well as other active ingredients in order to obtain special effects.

Such anthelmintic compositions employed by the end user likewise constitute an object of the present invention.

In each of the methods of controlling pests and in each of the pesticidal compositions of the invention, the compounds of formula I may be employed in all tautomeric forms or mixtures thereof or in the form of their salts.

The invention also relates to a prophylactic method of protecting animals against parasitic helminths, which process comprises administering to the animals the compounds of formula I or the formulations thereof as an additive to the solid or liquid feed, or in solid or liquid form orally, by injection or parenterally.

The invention is illustrated in more detail by the following non-limitative Examples.

1. PREPARATORY EXAMPLES 1.1

4-(5-Trifluoromethylpyrid-2-yloxy)phenylisocyanate 20.3 g (0.08 mol) of 4-(5-trifluoromethylpyrid-2-yloxy)aniline are dissolved in 200 ml of dry chlorobenzene. This solution is cooled to −20° C. and rapidly added a solution of 3.7 g of gaseous HCl in 80 ml of dry chlorobenzene. The resultant crystalline slurry is cooled to −30° C. and a strong flow of about 40 g of phosgene is introduced over 1 hour. The addition of phosgene is then discontinued and the reaction mixture is stirred for 1 hour at 20° C. and subsequently for 1 hour in an oil bath at 110° C. A clear solution forms which is then cooled in a stream of nitrogen and, with stirring, excess phosgene is expelled with nitrogen. First the chlorobenzene is distilled off under normal pressure and then the isocyanate is distilled off under a high vaccum. Boiling point 105°–107° C./0.03 mbar; yield >90%.

1.2

1,3-Dimethyl-5-[4-chloro-2-(2,6-dichlorophenoxy)-phenylcarbamoyl]-2-thiobarbituric acid (a) 1,3-Dimethyl-5-ethoxycarbonyl-2-thiobarbituric acid 155 g (0.9 mol) of 1,3-dimethyl-2-thiobarbituric acid, 88,3 g (1.12 mol) of pyridine and 9 g of 4-dimethylaminopyridine are dissolved in 660 ml of dichloromethane and the solution is cooled to 0° C. Then 102 g (0.94 mol) of ethyl chloroformate are added dropwise over 1 hour. The mixture is subsequently stirred for 12 hours at 0° C., then allowed to warm to room temperature and worked up after a further 7 hours as follows. 600 ml of dichloromethane are added and the solution is washed with three 1000 ml portions of water, dried over $Na_2SO_4$ and the solvent is evaporated off. The crude product is recrystallised from ethanol. Melting point 90°–93° C.

(b)

2.5 g (10 mmol) of 1,3-dimethyl-5-ethoxycarbonyl-2-thiobarbituric acid, 2.9 g (10 mmol) of 4-chloro-2-(2,6-dichlorophenoxy)aniline, 40 ml of ethanol and 3 ml of dimethylformamide are mixed and then boiled under reflux with stirring for 6 hours. The reaction mixture is then cooled and the resultant crystalline precipitate is isolated by filtration. If necessary, the crystalline precipitate can be recrystallised from a mixture of dioxane and ethanol. Melting point 254°–257° C.

1.3

1,3-Dimethyl-5-[4-(5-trifluoromethylpyrid-2-yloxy)-phenylcarbamoyl]-2-thiobarbituric acid 2.5 g (10 mmol) of 1,3-dimethyl-5-ethoxycarbonyl-2-thiobarbituric acid, 2,55 g (10 mmol) of 4-(5-trifluoromethylpyrid-2-yloxy)aniline and 5 ml of dimethylformamide are stirred for 6 hours at 118° C. The reaction mixture is then cooled, triturated with water and the crystalline precipitate is isolated by filtration. The crude product is recrystallised from ethanol. Melting point 156°–158° C.

1.4

1-Methyl-3-ethyl-5-[4-chloro-2-(4-chlorophenoxy)-phenylcarbamoyl]-2-thiobarbituric acid 3.4 g (20 mmol) of 1-methyl-3-ethyl-2-thiobarbituric acid are suspended in 80 ml of xylene. 1 g (8 mmol) of triethylamine is added, the mixture is heated to 40° C. and a solution of 5.6 g (20 mmol) of 4-chloro-2-(4-chlorophenoxy)phenylisocyanate in 30 ml of xylene is added dropwise with stirring at 40° C. The mixture is subsequently stirred for 2 hours at 40° C. and then cooled. 50 ml of 2N HCl are added, the crystalline precipitate is isolated by filtration, washed with water and dried at 80° C., affording a product with a melting point of 250°–251° C.

1.5

1,3-Dimethyl-5-[4-chloro-2-(2,6-dichlorophenoxy)-phenylcarbamoyl]-2-thiobarbituric acid 15.5 g (0.09 mol) of 1,3-dimethyl-2-thiobarbituric acid, 8.8 g (1.1 mol) of pyridine and 0.9 g of 4-dimethylaminopyridine are dissolved in 65 ml of dichloromethane and the solution is cooled to 0° C. Then 10.2 g (0.094 mol) of ethyl chloroformate are added dropwise over 1 hours. The mixture is stirred for 12 hours at 0° C. and then for 7 hours at room temperature. The bulk of the solvent is evaporated off, a solution of 26.1 g (0.09 mol) of 4-chloro-2-(2,6-dichlorophenoxy)aniline in 360 ml of ethanol and 30 ml of dimethylformamide is added and the mixture is boiled under reflux with stirring for 6 hours. The reaction mixture is then cooled and the resultant crystalline precipitate is isolated by filtration and, if necessary, is recrystallised from dioxane/ethanol. Melting point 254°–257° C.

1.6

1,3-Dimethyl-5-[4-(2-chloro-4-trifluoromethylphenoxy)-2,6-dimethylphenylcarbamoyl]-2-thiobarbituric acid (a)

2.7 g (0.025 mol) of ethyl chlororformate are added at 0° C. to 6.4 g (0.02 mol) of 2,6-dimethyl-4-(2-chloro-4-trifluoromethylphenoxy)benzoic acid in 50 ml of acetone and then 2.2 g (0.022 mol) of triethylamine are added over 15 minutes. Also at 0° C., a solution of 2.0 g (0.03 mol) of sodium azide in 7 ml of water is then added. The mixture is stirred for 3 hours at 0° C., then poured into 100 ml of ice water and extracted with toluene. The toluene phase, which contains the product 2,6-dimethyl-4-(2-chloro-4-trifluoromethylphenoxy)-benzoylazide, is dried over $Na_2SO_4$.

(b)

3.44 g (0.02 mol) of 1,3-dimethyl-2-thiobarbituric acid and 2.0 g (0.02 mol) of triethylamine are dissolved in 40 ml of toluene and the solution is heated to 90° C. At this temperature, the entire solution of the 2,6-dimethyl-4-(2-chloro-4-trifluoromethylphenoxy)benzoylazide in toluene obtained in step (a) is added dropwise. The rate of addition is dependent on the degree of nitrogen evolution. When the dropwise addition is complete, the temperature is increased to reflux and the mixture is boiled until no more nitrogen evolves. The mixture is then cooled and the precipitate is isolated by filtration and washed with a small amount of ethanol. The resultant triethylammonium salt of thiobarbituric acid is suspended in 1N HCl, isolated by filtration and then thoroughly washed with water, affording the final product. Melting point 171°–173° C.

1.7

1,3-Dimethyl-5-[3-(2-chloro-4-trifluoromethylphenoxy)-4-methoxyphenylcarbamoyl]-2-thiobarbituric acid (a)

A mixture of 33.6 g (0.2 mol) of 3-hydroxy-4-methoxybenzoic acid and 26.8 g (0.4 mol) of potassium hydroxide (85%) in 200 ml of toluene and 200 ml of dimethyl sulfoxide is dewatered at 140° C. in a sulfonating flask equipped with a water separator. The toluene is distilled off and the mixture is then cooled to 90° C. and 43 g (0.2 mol) of 3,4-dichlorobenzotrifluoride, 1.1 g of potassium iodide and 0.2 g of copper filings in 20 ml of dimethyl sulfoxide are added. The mixture is kept for 30 hours at 150° C. and the solvent is then distilled off under a high vacuum. The residue is dissolved in 250 ml of water, the solution is filtered, the filtrate is acidified with 100 ml of 2N HCl in 200 g of ice and the precipitate obtained is filtered with suction, then washed with water and vacuum-dried at 80° C., affording 58 g of 3-(2-chloro-4-trifluoromethylphenoxy)-4-methoxybenzoic acid. Melting point 162°–165° C.

(b)

2.7 g (0.025 mol) of ethyl chloroformate are added at 0° C. to 6.4 g (0.02 mol) of 3-(2-chloro-4-trifluoromethylphenoxy)-4-methoxybenzoic acid in 50 ml of acetone and then 2.2 g (0.022 mol) of triethylamine are added over 15 minutes. Also at 0° C., a solution of 2.0 g (0.03 mol) of sodium azide in 7 ml of water is then added. The mixture is stirred for 3 hours at 0° C., then poured into 100 ml of ice water and extracted with toluene. The toluene phase, which contains the product 3-(2-chloro-4-trifluoromethylphenoxy)-4-methoxybenzoylazide, is dried over $Na_2SO_4$.

(c)

3.44 g (0.02 mol) of 1,3-dimethyl-2-thiobarbituric acid and 2.0 g (0.02 mol) of triethylamine are dissolved in 40 ml of toluene and the solution is heated to 90° C. As this temperature, the entire solution of the 3-(2-chloro-4-trifluoromethylphenoxy)-4-methoxybenzoylazide in toluene obtained in step (b) is added. The rate of addition is dependent on the degree of nitrogen evolution. When the dropwise addition is complete, the temperature is increased to reflux and the mixture is boiled until no more nitrogen evolves. The mixture is then cooled and the precipitate is isolated by filtration and washed with a small amount of ethanol. The resultant triethylammonium salt of thiobarbituric acid is suspended in 1N HCl, isolated by filtration and then thoroughly washed with water, affording the final product. Melting point 165°–168° C.

1.8
1.3-Dimethyl-5-[3-(3,5-dichloropyrid-2-yloxy)-4-methoxyphenylcarbamoyl]-2-thiobarbituric acid (a)

A mixture of 14.0 g (0.1 mol) of 5-amino-2-methoxyphenol and 6.7 g (0.1 mol) of potassium hydroxide (85%) in 100 ml of toluene and 100 ml of dimethyl sulfoxide is dewatered at 150° C. in a sulfonating flask equipped with a water separator. After 3 hours the toluene is distilled off, the mixture is cooled to 80° C. and 18.2 g (0.1 mol) of 2,3,5-trichloropyridine in 25 ml of dimethyl sulfoxide are added. The mixture is stirred for 3 hours at 120° C. and then cooled and 5 ml of acetic acid are added. After distillation under a high vacuum, the residue is extracted with 200 ml of water and 300 ml of methylene chloride. The organic phase affords 28 g of 3-(3,5-dichloropyrid-2-yloxy)-4-methoxyaniline as congealing oil. Melting point 95°–105° C.

(b)

3.7 g (15 mmol) of 1,3-dimethyl-5-ethoxycarbonyl-2-thiobarbituric acid, 4,3 g (15 mmol) of 3-(3,5-dichloropyrid-2-yloxy)-4-methoxy aniline and 13 ml of dimethylformamide are stirred for 20 hours at 60° C. The reaction mixture is then cooled, triturated with water and the crystalline precipitate is isolated by filtration. The crude product is suspended in ethanol and filtered with suction. Melting point 179°–180° C.

(c) 1.9
1,3-Dimethyl-5-[4-(2-chloro-4-trifluoromethylphenoxy)-3-methoxyphenylcarbamoyl]-2-thiobarbituric acid 3.7 g (15 mmol) of 1,3-dimethyl-5-ethoxycarbonyl-2-thiobarbituric acid, 4.8 g (15 mmol) of 4-(2-chloro-4-trifluoromethylphenoxy)-3-methoxyaniline and 13 ml of dimethylformamide are stirred for 20 hours at 60° C. The mixture is then cooled, triturated with water and the crystalline precipitate is isolated by filtration. The crude product is suspended in ethanol and filtered with suction. Melting point 178°–182° C.

TABLE 1

Compounds of the formula

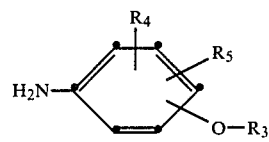

| Compound | $R_4$ | $R_5$ | $-OR_3$ | Physical data [°C.] [mbar] |
|---|---|---|---|---|
| 3.1 | H | H | 4-O—$C_6H_4$—$CF_3$(3) | oily |
| 3.2 | 2-$CH_3$ | 6-$CH_3$ | 4-O—$C_6H_4$—$CF_3$(4) | b.p. 126/0.01 |
| 3.3 | 2-$CH_3$ | 6-$CH_3$ | 4-O—$C_6H_3$—Cl(3)-$CF_3$(4) | b.p. 135/0.01 |
| 3.4 | 2-$CH_3$ | 6-$CH_3$ | 4-O—$C_6H_3$—Cl(2)-$CF_3$(4) | m.p. 104–106 |
| 3.5 | 2-$C_3H_7$iso | H | 4-O—$C_6H_4$—$CF_3$(4) | b.p. 127/0.01 |
| 3.6 | 2-$C_3H_7$iso | H | 4-O—$C_6H_4$—$CF_3$(3) | b.p. 140/0.02 |
| 3.7 | 2-$C_3H_7$iso | H | 4-O—$C_6H_3$—Cl(3)-$CF_3$(4) | b.p. 135–150/0.01 |
| 3.8 | H | H | 4-O—$C_6H_4$—$CF_3$(4) | m.p. 77–79 |
| 3.9 | 2-$CH_3$ | H | 4-O—$C_6H_4$—$CF_3$(4) | m.p. 120/0.01 |
| 3.10 | H | H | 4-O—pyridyl(2)-$CF_3$(5) | oily |
| 3.11 | H | H | 4-O—pyridyl(2)-Cl(3)-$CF_3$(5) | b.p. 133–135/0.03 |
| 3.12 | 2-$C_3H_7$iso | H | 4-O—pyridyl(2)-$CF_3$(5) | b.p. 121–126/0.02 |
| 3.13 | H | H | 4-O—pyridyl(2)-$NO_2$(3) | m.p. 110–112 |
| 3.14 | H | H | 4-O—pyridyl(2)-$NO_2$(5) | oily |
| 3.15 | H | H | 4-O—$C_6H_3$—$CF_3$(3)-$NO_2$(4) | oily |
| 3.16 | H | H | 4-O—$C_6H_3$—$CF_3$(2)-$NO_2$(4) | oily |
| 3.17 | H | H | 4-O—$C_6H_3$—$CF_3$(4)-$NO_2$(2) | oily |
| 3.18 | 2-$CH_3$ | 6-$CH_3$ | 4-O—$C_6H_3$—$CF_3$(4)-$NO_2$(2) | oily |
| 3.19 | 2-$CH_3$ | 6-$CH_3$ | 4-O—pyridyl(2)-$CF_3$(5) | b.p. 125–127/0.04 |
| 3.20 | H | H | 4-O—pyridyl(2)-$Cl_2$(3,5) | m.p. 72–74 |
| 3.21 | 4-$OCH_3$ | H | 3-O—pyridyl(2)-$Cl_2$(3,5) | m.p. 100–105 |
| 3.22 | 3-$OCH_3$ | H | 4-O—$C_6H_3$-Cl(2)-$CF_3$(4) | oily |
| 3.23 | H | H | 4-O—pyridyl(2)-Cl(5)-F(3) | |
| 3.24 | 3-$OCH_3$ | H | 4-O—pyridyl(2)-Cl(5)-F(3) | |
| 3.25 | 4-$OCH_3$ | H | 3-O—pyridyl(2)-Cl(5)-F(3) | |

TABLE 2

Compound of the formula

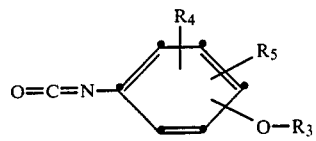

| Compound | R4 | R5 | —OR3 | Physical data [°C.] [mbar] |
|---|---|---|---|---|
| 5.1 | H | H | 4-O—C6H4—CF3(3) | oily |
| 5.2 | 2-CH3 | 6-CH3 | 4-O—C6H4—CF3(4) | b.p. 118/0.03 |
| 5.3 | 2-C3H7iso | H | 4-O—C6H4—CF3(4) | b.p. 123/0.2 |
| 5.4 | 2-C3H7iso | H | 4-O—C6H4—CF3(3) | b.p. 107–110/0.05 |
| 5.5 | H | H | 4-O—C6H4—CF3(4) | b.p. 118–120/0.08 |
| 5.6 | H | H | 4-O—pyridyl(2)-Cl(3)-CF3(5) | oily |
| 5.7 | H | H | 4-O—pyridyl(2)-Cl2(3,5) | m.p. 65–66 |

TABLE 3

Compounds of the formula

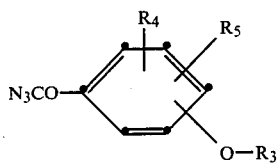

| Compound | R4 | R5 | —OR3 | Physical data [°C.] |
|---|---|---|---|---|
| 6.1 | 4-OCH3 | H | 3-O—pyridyl(2)—Cl2(3,5) | |
| 6.2 | 4-OCH3 | H | 3-O—C6H3—Cl(2)—CF3(4) | |
| 6.3 | 3-OCH3 | H | 4-O—C6H3—Cl(2)—CF3(4) | |

Examples of benzoic acid derivatives of the formula

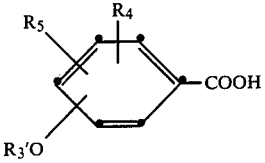

which are suitable for the preparation of compounds of formula VI are: 3-(3,5-dichloropyrid-2-yloxy)-4-methoxybenzoic acid (m.p. 217°–218° C.) and 3-(2-chloro-4-trifluoromethylphenoxy)-4-methoxybenzoic acid (m.p. 162°–165° C.; Example 1.7a ) and 4-(2-chloro-4-trifluoromethylphenoxy)-3-methoxybenzoic acid (m.p. 174°–176° C.).

TABLE 4

Compounds of the formula

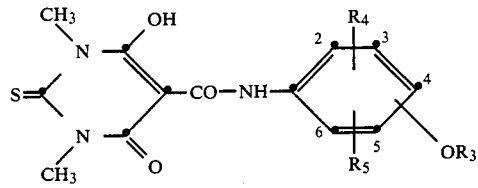

| Compound | R1 | R2 | R4 | R5 | —OR3 | Physical data m.p. [°C.] |
|---|---|---|---|---|---|---|
| 1.1 | CH3 | CH3 | 4-Cl | H | 2-O—C6H3—Cl2(2,6) | 254–257 |
| 1.2 | CH3 | CH3 | 4-Cl | H | 2-O—C6H4—F(4) | 244–247 |
| 1.3 | CH3 | CH3 | H | H | 4-O—C6H4—(CH2CN)(3) | 167–170 |
| 1.4 | CH3 | CH3 | 3-Cl | 5-Cl | 4-O—pyridyl(2)-Cl(3)-CF3(5) | 231–233 |
| 1.5 | CH3 | CH3 | H | H | 4-O—C6H4—CF3(3) | 148–149 |
| 1.6 | CH3 | CH3 | 2-CH3 | 6-CH3 | 4-O—C6H4—CF3(4) | 183–184 |
| 1.7 | CH3 | CH3 | 2-CH3 | 6-CH3 | 4-O—C6H3—Cl(2)-CF3(4) | 171–173 |
| 1.8 | CH3 | CH3 | 2-C3H7iso | H | 4-O—C6H4—CF3(4) | 162–163 |
| 1.9 | CH3 | CH3 | 2-C3H7iso | H | 4-O—C6H4—CF3(3) | 111–113 |
| 1.10 | CH3 | CH3 | 2-C3H7iso | H | 4-O—C6H3—Cl(3)-CF3(4) | 130–136 |
| 1.11 | CH3 | CH3 | H | H | 4-O—C6H4—CF3(4) | 165–170 |
| 1.12 | CH3 | CH3 | 2-CH3 | H | 4-O—C6H4—CF3(4) | 168–176 |
| 1.13 | CH3 | CH3 | H | H | 4-O—pyridyl(2)-CF3(5). | 156–158 |
| 1.14 | CH3 | CH3 | H | H | 4-O—pyridyl(2)-CF3(5) N(C2H5)3 | 102–105 |
| 1.15 | CH3 | CH3 | H | H | 4-O—pyridyl(2)-Cl(3)-CF3(5) | 153–154 |
| 1.16 | CH3 | CH3 | 2-C3H7iso | H | 4-O—pyridyl(2)-CF3(5) | 189–190 |
| 1.17 | CH3 | CH3 | H | H | 4-O—pyridyl(2)-NO2(3) | 210–213 |
| 1.18 | CH3 | CH3 | H | H | 4-O—pyridyl(2)-NO2(5) | 198–200 |
| 1.19 | CH3 | CH3 | H | H | 4-O—C6H3—CF3(3)-NO2(4) | 187–189 |
| 1.20 | CH3 | CH3 | H | H | 4-O—C6H3—CF3(2)-NO2(4) | 193–195 |
| 1.21 | CH3 | CH3 | H | H | 4-O—C6H3—CF3(4)-NO2(2) | 173–174 |

TABLE 4-continued

Compounds of the formula $$\text{structure with } CH_3\text{-N, S, N-}CH_3 \text{ ring, }-C(OH)=\text{, }-CO-NH-\text{phenyl with } R_4, R_5, OR_3$$

| Compound | $R_1$ | $R_2$ | $R_4$ | $R_5$ | $-OR_3$ | Physical data m.p. [°C.] |
|---|---|---|---|---|---|---|
| 1.22 | $CH_3$ | $CH_3$ | 2-$CH_3$ | 6-$CH_3$ | 4-O—$C_6H_3$—$CF_3$(4)-$NO_2$(2) | 172–174 |
| 1.23 | $CH_3$ | $CH_3$ | 2-$CH_3$ | 6-$CH_3$ | 4-O—pyridyl(2)-$CF_3$(5) | 210–211 |
| 1.24 | $CH_3$ | $CH_3$ | H | H | 4-O—pyridyl(2)-$Cl_2$-(3,5) | 177–178 |
| 1.25 | $CH_3$ | $CH_3$ | H | H | 4-O—pyridyl(2)-Cl-(5)-F(3) | 185–187 |
| 1.26 | $CH_3$ | $CH_3$ | H | H | 4-O—pyridyl(2)-$F_2$-(3,5) | — |
| 1.27 | $CH_3$ | $CH_3$ | 4-$OCH_3$ | H | 3-O—pyridyl(2)-$Cl_2$(3,5) | 179–180 |
| 1.28 | $CH_3$ | $CH_3$ | 3-$OCH_3$ | H | 4-O—pyridyl(2)-$Cl_2$(3,5) | 179–180 |
| 1.29 | $CH_3$ | $CH_3$ | 4-$OCH_3$ | H | 3-O—$C_6H_3$—Cl(2)-$CF_3$(4) | 165–168 |
| 1.30 | $CH_3$ | $CH_3$ | 3-$OCH_3$ | H | 4-O—$C_6H_3$—Cl(2)-$CF_3$(4) | 178–182 |
| 1.31 | $CH_3$ | $CH_3$ | 3-$OCH_3$ | H | 4-O—pyridyl(2)-Cl(3)-$CF_3$(5) | 205–207 |
| 1.32 | $CH_3$ | $CH_3$ | 4-$OCH_3$ | H | 3-O—pyridyl(2)-Cl(3)-$CF_3$(5) | 195–197 |
| 1.33 | $CH_3$ | $CH_3$ | 3-$OCH_3$ | H | 4-O—pyridyl(2)-Cl(5)-F(3) | 170–172 |
| 1.34 | $CH_3$ | $CH_3$ | 4-$OCH_3$ | H | 3-O—pyridyl(2)-Cl(5)-F(3) | 186–189 |
| 1.35 | $CH_3$ | $CH_3$ | 3-$OCH_3$ | H | 4-O—pyridyl(2)-$CF_3$(5) | 143–145 |

Formulation Examples (throughout, percentages are by weight)

| 2.1 Emulsifiable concentrates | (a) | (b) | (c) |
|---|---|---|---|
| a compound of Table 4 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| 2.2 Emulsifiable concentrates | (a) | (b) | (c) |
|---|---|---|---|
| a compound of Table 4 | 10% | 8% | 60% |
| octylphenol polyethylene glycol ether (4–5 moles of ethylene oxide) | 3% | 3% | 2% |
| calcium dodecylbenzenesulfonate | 3% | 4% | 4% |
| castor oil polyglcol ether (35 moles of ethylene oxide) | 4% | 5% | 4% |
| cyclohexanone | 30% | 40% | 15% |
| xylene mixture | 50% | 40% | 15% |

Emulsions of any required concentration can be obtained from this concentrate by dilution with water.

| 2.3. Suspension concentrate | |
|---|---|
| a compound of Table 4 | 40% |
| ethylene glycol | 10% |
| nonylphenol polyethylene glycol (15 moles of ethlene oxide) | 6% |
| sodium lignosulfonate | 10% |
| carboxymethyl cellulose | 1% |

| 2.3. Suspension concentrate -continued | |
|---|---|
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

| 2.4 Wettable powders | (a) | (b) | (c) |
|---|---|---|---|
| a compound of Table 4 | 25% | 50% | 75% |
| sodium lignosulfonate | 5% | 5% | — |
| oleic acid | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.5 Dusts | (a) | (b) |
|---|---|---|
| a compound of Table 4 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| 2.6 Granulates | (a) | (b) |
|---|---|---|
| a compound of Table 4 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo. Such granulates can be mixed with the cattle feed.

| 2.7 Granulate | |
|---|---|
| a compound of Table 4 | 10% |
| sodium lignosulfonate | 2% |
| carboxymethyl cellulose | 1% |
| kaolin | 87% |

The active ingredient is mixed and ground with the adjuvants, and the mixture is subsequently moistened with water. The mixture is extruded and then dried in a stream of air.

| 2.8 Granulate | |
|---|---|
| a compound of Table 4 | 3% |
| polyethlene glycol 200 | 3% |
| kaolin | 94% |

The finely ground active ingredient is uniformly applied, in a mixer, to the kaolin moistened with polyethylene glycol. Non-dusty coated granulates are obtained in this manner.

| 2.9 Tablets or boluses | | |
|---|---|---|
| I | a compound of Table 4 | 33.0% |
| | methyl cellulose | 0.80% |
| | highly dispersed silic acid | 0.80% |
| | maize starch | 8.40% |
| II | crystalline lactose | 22.50% |
| | maize starch | 17.00% |
| | microcrystalline cellulose | 16.50% |
| | magnesium stearate | 1.00% |

I The methyl cellulose is stirred in water and allowed to swell. Then the silicic acid is stirred in to give a homogeneous suspension. The compound of formula I and the maize starch are mixed and the aqueous suspension is added to the mix, which is kneaded to a paste. This paste is granulated through a 12M sieve and the granulate is dried.

II All 4 adjuvants are thoroughly mixed.

III Phases I and II are mixed and compressed to tablets or boluses.

3. BIOLOGICAL EXAMPLES

The following test procedures are employed to demonstrate the anthelmintic activity of the compounds of formula I:

3.1 Trial with sheep infected with nematodes such as Haemonchus contortus and Trichostrongylus colubriformis The test compound is administered in the form of a suspension with a stomach probe or by intraruminal injection to sheep which have been artificially infected beforehand with nematodes such as *Haemonchus contortus* and *Trichostrongylus colubriformis*. One to three animals are used for each trial and for each dose. Each sheep is treated with only a single dose. A first evaluation is made by comparing the number of worm eggs excreted in the faeces of the sheep before and after treatment. The sheep are slaughtered and dissected 7 to 10 days after treatment. Evaluation is made by counting the number of worms remaining in the intestine after treatment. Untreated sheep infected simultaneously and in the same manner are used as controls.

In this trial, compounds of formula I reduce nematode infestation substantially. For example the following compounds reduce nematode infestation by at least 90% when administered at a dose of 20 mg per kg of body weight: 1.2, 1.5, 1.7, 1.9, 1.11, 1.13, 1.14, 1.15, 1.16, 1.19, 1.20, 1.21, 1.22, 1.23, 1.24, 1.27, 1.28, 1.29 and 1.30. Individual compounds also produce this result even when administered at a much lower dose, e.g. 12 mg per kg of body weight or lower.

3.2 Trial with sheep infected with cestodes such as Moniezia benedeni

The test compound is administered in the form of a suspension with a stomach probe or by intraruminal injection to sheep which have been artificially infected beforehand with cestodes such as *Moniezia benedeni*. Three animals are used for each trial and for each dose. Each sheep is treated with only a single dose. The sheep are slaughtered and dissected 7 to 10 days after treatment. Evaluation is made by counting the number of worms remaining in the intestine after treatment. Untreated sheep infected simultaneously and in the same manner are used as controls. In this trial, compounds of Table 4, e.g. compounds 1.15, 1.20 and 1.21, reduce cestode infestation by 90% at doses of less than 20 mg/kg of body weight.

3.3 Trial with sheep infected with Fasciola hepatica

The test compound is administered in the form of a suspension with a stomach probe or by intraruminal injection to sheep which have been artificially infected beforehand with *Fasciola hepatica*. Three animals are used for each trial and for each dose. Each sheep is treated with only a single dose. A firts evaluation is made by comparing the number of worm eggs excreted in the faeces of the sheep before and after treatment. The sheep are slaughtered and dissected 3 to 4 weeks after treatment. Evaluation is made by counting the number of liver flukes remaining in the hepatic ducts after treatment. Untreated sheep infected simultaneously and in the same manner are used as controls. The difference in the number of flukes found in both groups indicates the degree of activity of the tested compound.

In this trial, compounds of Table 4 are at least 95% effective against *Fasciola hepatica* at doses of less than 20 mg/kg of body weight. Among these compounds, compound 1.11 is fully effective (100% kill) against *Fasciola hepatica* at a dose of 12 mg/kg of body weight.

What is claimed is:

1. A 5-phenylcarbamoylthiobarbituric acid compound of the formula I

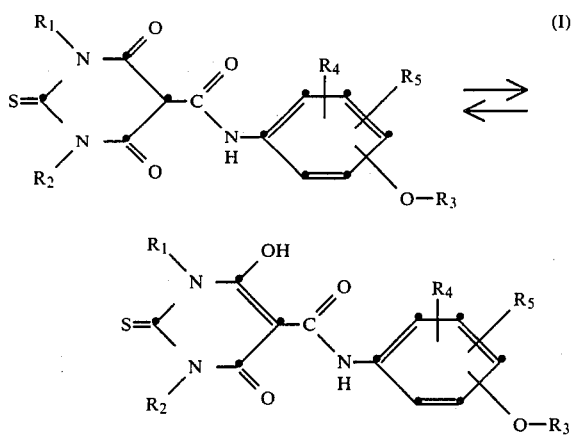

wherein
R$_1$ and R$_2$ are each independently C$_1$-C$_5$alkyl or methoxy,

R$_3$ is unsubstituted pyridyl or pyridyl which is substituted by 1 to 3 identical or different members selected from the group consisting of C$_1$-C$_5$alkyl, halogen, nitro and C$_1$-C$_5$haloalkyl having 1 to 5 halogen atoms, and R$_4$ and R$_5$ are each independently hydrogen, halogen, C$_1$-C$_5$alkyl, C$_1$-C$_5$haloalkyl having 1 to 3 halogen atoms, or are C$_1$-C$_3$alkoxy or nitro, or a tautomer or salt thereof.

2. A compound according to claim 1 wherein R$_4$ and R$_5$ are each independently hydrogen, halogen, C$_1$-C$_5$-alkyl, nitro or C$_1$-C$_2$-haloalkyl having 1 to 3 halogen atoms.

3. A compound according to claim 1, wherein R$_1$ is methyl, ethyl or methoxy, R$_2$ is methyl, R$_3$ is unsubstituted pyridyl or pyridyl which is substituted by 1 or 2 identical or different members selected from the group consisting of C$_1$-C$_5$alkyl, halogen, nitro and C$_1$-C$_5$-haloalkyl containing 1 to 3 halogen atoms and R$_4$ and R$_5$ are each independently hydrogen, C$_1$-C$_5$alkyl or halogen.

4. A compound according to claim 1, wherein R$_1$ is methyl or methoxy, R$_2$ is methyl, R$_3$ is pyridyl which is substituted by methyl, chlorine, fluorine or trifluoromethyl and R$_4$ and R$_5$ are each independently hydrogen, C$_1$-C$_3$alkyl, chlorine or nitro.

5. A compound according to claim 1, wherein R$_1$ is methyl or methoxy, R$_2$ is methyl, R$_3$ is pyridyl which is substituted by methyl, chlorine or trifluoromethyl and R$_4$ and R$_5$ are each independently hydrogen or C$_1$-C$_3$alkyl and the radical —O—R$_3$ is in the 2- or 4-position.

6. A compound according to claim 1, wherein R$_1$ is methyl or ethyl, R$_2$ is methyl, R$_3$ is 2-pyridyl which is substituted by 1 or 2 identical or different members selected from the group consisting of fluorine, chlorine, nitro and trifluoromethyl, R$_4$ is hydrogen, chlorine, methyl, isopropyl or methoxy and R$_5$ is hydrogen, chlorine or methyl, or a triethylamine salt thereof.

7. A compound according to claim 1, wherein each of R$_1$ and R$_2$ is methyl, R$_3$ is 2-pyridyl which is substituted by 1 or 2 identical or different members selected from the group consisting of chlorine and trifluoromethyl, R$_4$ is hdyrogen, methyl, isopropyl or methoxy and R$_5$ is hydrogen or methyl, the radical —OR$_3$ being in meta or para-position to the nitrogen atom of the carbamoyl group, or a triethylamine salt thereof.

8. A compound according to claim 1, wherein each of R$_1$ and R$_2$ is methyl, R$_3$ is 2-pyridyl which is substituted by 1 or 2 identical or different members selected from the group consisting of chlorine and trifluoromethyl, R$_4$ is hydrogen or methoxy and R$_5$ is hydrogen, the radical —OR$_3$ being in meta- or para-position to the nitrogen atom of the carbamoyl group.

9. A compound selected from the group consisting of
1,3-dimethyl-5-[2-isopropyl-4-(5-trifluoromethylpyrid-2-yloxy)phenylcarbamoyl]-2-thiobarbituric acid,
1,3-dimethyl-5-[4-(5-trifluoromethylpyrid-2-yloxy)-phenylcarbamoyl]-2-thiobarbituric acid, triethylamine salt,
1,3-dimethyl-5-[4-(3-chloro-5-trifluoromethylpyrid-2-yloxy)phenylcarbamoyl]-2-thiobarbituric acid,
1,3-dimethyl-5-[2,6-dimethyl-4-(5-trifluoromethylpyrid-2-yloxy)phenylcarbamoyl]-2-thiobarbituric acid and
1,3-dimethyl-5-[4-(3,5-dichloropyrid-2-yloxy)phenylcarbamoyl]-2-thiobarbituric acid.

10. 1,3-Dimethyl-5-[4-(5-trifluoromethylpyrid-2-yloxy)phenylcarbamoyl]-2-thiobarbituric acid.

11. 1,3-Dimethyl-5-[4-methoxy-3-(3,5-dichloropyrid-2-yloxy)phenylcarbamoyl]-2-thiobarbituric acid according to claim 1.

12. An anthelmintic composition which contains, as active ingredient, at least one compound of formula I according to claim 1, or a tautomer or salt thereof, together with carriers and further adjuvants.

13. A method of controlling parasitic helminths, which comprises administering to an animal an anthelmintically effective amount of a compound of formula I according to claim 1.

* * * * *